(12) United States Patent
Kondo et al.

(10) Patent No.: US 8,912,497 B2
(45) Date of Patent: Dec. 16, 2014

(54) MEASUREMENT STRUCTURE, METHOD OF MANUFACTURING SAME, AND MEASURING METHOD USING SAME

(71) Applicant: Murata Manufacturing Co., Ltd., Nagaokakyo-Shi, Kyoto-fu (JP)

(72) Inventors: Takashi Kondo, Nagaokakyo (JP); Seiji Kamba, Nagaokakyo (JP)

(73) Assignee: Murata Manufacturing Co., Ltd., Nagaokakyo-Shi (JP)

( * ) Notice: Subject to any disclaimer, the term of this patent is extended or adjusted under 35 U.S.C. 154(b) by 19 days.

(21) Appl. No.: 14/041,145

(22) Filed: Sep. 30, 2013

(65) Prior Publication Data

US 2014/0021353 A1  Jan. 23, 2014

Related U.S. Application Data

(63) Continuation of application No. PCT/JP2011/077361, filed on Nov. 28, 2011.

(30) Foreign Application Priority Data

Mar. 31, 2011 (JP) ................................. 2011-078364

(51) Int. Cl.
*G01N 21/01* (2006.01)
*G01J 3/02* (2006.01)
*G01N 21/35* (2014.01)
*G01J 3/42* (2006.01)

(52) U.S. Cl.
CPC ........... *G01J 3/0267* (2013.01); *G01N 21/3586* (2013.01); *G01J 3/42* (2013.01)
USPC ...................................................... 250/341.1

(58) Field of Classification Search
CPC ................................................... G01N 21/3586
USPC ....................................................... 250/341.1
See application file for complete search history.

(56) References Cited

U.S. PATENT DOCUMENTS

2010/0025586 A1* 2/2010 Ogawa et al. .............. 250/341.1
2011/0017910 A1* 1/2011 Nagel ........................ 250/338.4

FOREIGN PATENT DOCUMENTS

JP  2007-010366 A   1/2007
JP  2009-019925 A   1/2009
WO  WO-2011-013452 A1  2/2011

OTHER PUBLICATIONS

PCT/JP2011/077361 International Search Report dated Feb. 28, 2012.

* cited by examiner

*Primary Examiner* — Constantine Hannaher
(74) *Attorney, Agent, or Firm* — Dickstein Shapiro LLP

(57) ABSTRACT

A measurement structure including an aperture array structure made of a metal and having a plurality of aperture portions, and a support base supporting the aperture array structure. The measurement structure is used in a measuring method by applying an electromagnetic wave to the measurement structure on which a specimen is held, detecting frequency characteristics of the electromagnetic wave transmitted through the measurement structure or reflected by the measurement structure, and measuring characteristics of the specimen. At least a first part of a surface of the aperture array structure proximal to the support base is joined to the support base, and at least a second part of the surface of the aperture array structure defines at least part of the plurality of aperture portions, the second part of the surface being proximal to the support base and not in contact with the support base.

18 Claims, 10 Drawing Sheets

MEASUREMENT STRUCTURE, METHOD OF MANUFACTURING SAME, AND MEASURING METHOD USING SAME

CROSS REFERENCE TO RELATED APPLICATIONS

The present application is a continuation of International application No. PCT/JP2011/077361, filed Nov. 28, 2011, which claims priority to Japanese Patent Application No. 2011-078364, filed Mar. 31, 2011, the entire contents of each of which are incorporated herein by reference.

FIELD OF THE INVENTION

The present invention relates to a measurement structure, a method of manufacturing the measurement structure, and a measuring method using the measurement structure.

BACKGROUND OF THE INVENTION

With intent to analyze characteristics of a substance, a measuring method has hitherto been used which includes the steps of holding a specimen to be measured on an aperture array structure, applying an electromagnetic wave to the aperture array structure on which the specimen is held, and analyzing a transmittance spectrum of the electromagnetic wave, thereby measuring the characteristics of the specimen. One practical example is a method of applying a terahertz wave to a metal mesh filter, for example, to which a specimen, such as a protein, is attached, and analyzing a transmittance spectrum of the terahertz wave.

Through the studies made by the inventors, it is known that sensitivity in detection of the specimen has a tendency to increase by employing an electromagnetic wave of a shorter wavelength. In the case using the electromagnetic wave of the shorter wavelength, however, the thickness of the aperture array structure requires to be reduced, and it becomes the order of about 100 nm to 20 μm, for example. Forming such a thin metal mesh or the like in shape of several millimeters or several centimeters square in a not-flexing state is very difficult to realize in practice.

For that reason, when the aperture array structure being so thin is used, a support base (e.g., a resin film) to which the aperture array structure is bonded for fixation is needed in order to keep the aperture array structure in the not-flexing state.

Patent Document 1 (Japanese Unexamined Patent Application Publication No. 2007-010366) discloses a method of holding a specimen to be measured on an aperture array structure (e.g., a metal mesh) having an aperture region and on a base in close contact with the aperture array structure, applying an electromagnetic wave to the aperture array structure on which the specimen is held, and detecting the electromagnetic wave having transmitted through the aperture array structure, thereby measuring characteristics of the specimen based on a change of frequency characteristics, the change being caused due to the presence of the specimen. One of principal surfaces of the aperture array structure is in a state entirely bonded to the base. Furthermore, the base in Patent Document 1 is used to primarily to make the specimen adsorbed to the base. In some cases, a material capable of selectively adsorbing the specimen may be coated over the base in advance.

In the case using the support base mentioned above, however, a problem arises in that one 10b of principal surfaces 10a and 10b of an aperture array structure 1 is in a state entirely bonded to a support base 2 as illustrated in FIG. 14, and hence the specimen cannot be held on the one principal surface, whereby a region near the principal surface of the aperture array structure where sensitivity is maximum cannot be efficiently used for the measurement. Stated in another way, in the measuring method described above, a change of frequency characteristics is caused due to the interaction between an electromagnetic field localized on the surface of the aperture array structure and the specimen. The intensity of the localized electromagnetic field is maximal in regions near both the principal surfaces of the aperture array structure, and it attenuates exponentially as a distance from both the principal surfaces increases.

Patent Document 1: Japanese Unexamined Patent Application Publication No. 2007-010366

SUMMARY OF THE INVENTION

An object of the present invention is to provide a measurement structure, which can realize measurement of characteristics of a specimen with high sensitivity and high efficiency even when an amount of the specimen is very small, as well as a method of manufacturing the measurement structure, and a measuring method using the measurement structure.

The present invention provides a measurement structure comprising:

an aperture array structure made of a metal and including a plurality of aperture portions; and a support base supporting the aperture array structure, the measurement structure being used in a measuring method of applying an electromagnetic wave to the measurement structure on which a specimen to be measured is held, detecting frequency characteristics of the electromagnetic wave having transmitted through the measurement structure or the electromagnetic wave having been reflected by the measurement structure, and measuring characteristics of the specimen, wherein at least a part of a principal surface of the aperture array structure on side closer to the support base is joined to the support base, and at least a part of one of principal surfaces of the aperture portion in the aperture array structure, the one principal surface being positioned on side closer to the support base, is not contacted with the support base.

Preferably, the support base is made of a material containing silicon or a silicon compound as a main component.

Furthermore, the present invention provides a method of manufacturing the measurement structure mentioned above, the method comprising the steps of:

forming an aperture array structure, made of a metal and including a plurality of aperture portions, on a surface of a support base in form of a plate or a film; and cutting away the support base in a direction of thickness thereof to form one or more recesses with etching progressed through the aperture portions of the aperture array structure.

Still further, the present invention provides a measuring method comprising the steps of holding a specimen to be measured in aperture portions of the measurement structure mentioned above, and applying an electromagnetic wave to the measurement structure on which the specimen is held, detecting frequency characteristics of the electromagnetic wave having transmitted through the measurement structure or the electromagnetic wave having been reflected by the measurement structure, and measuring characteristics of the specimen.

According to the present invention, since a region near the principal surface of the aperture array structure where maximum detection sensitivity is obtained is kept in a vacant state not occupied by anything, the detection sensitivity is increased. Furthermore, since opposite sides of the region near the principal surface of the aperture array structure can be used to hold the specimen, the detection sensitivity can be further increased. Thus, even when an amount of the specimen is very small (or a thickness of the specimen from the aperture array structure is thin), characteristic measurement of the specimen can be realized with high sensitivity and high efficiency.

Moreover, since the measurement structure of the present invention can be fabricated through a step of cutting away the support base in the direction of thickness thereof with etching progressed through the aperture portions of the aperture array structure, it is easy to manufacture the aperture array structure by employing general-purpose semiconductor techniques such as the MEMS (Micro Electro Mechanical System) technique.

In addition, since the measurement structure of the present invention includes the one or more recesses in a surface of the support base on the side closer to the aperture array structure (i.e., in a portion of the support base, which portion is not contacted with one of the principal surfaces of the aperture portion in the aperture array structure, the one principal surface being positioned on the side closer to the support base), the recess can be advantageously utilized as a container for containing the specimen when the specimen (sample) is a liquid.

DETAILED DESCRIPTION OF THE PREFERRED EMBODIMENTS

Figure 1:
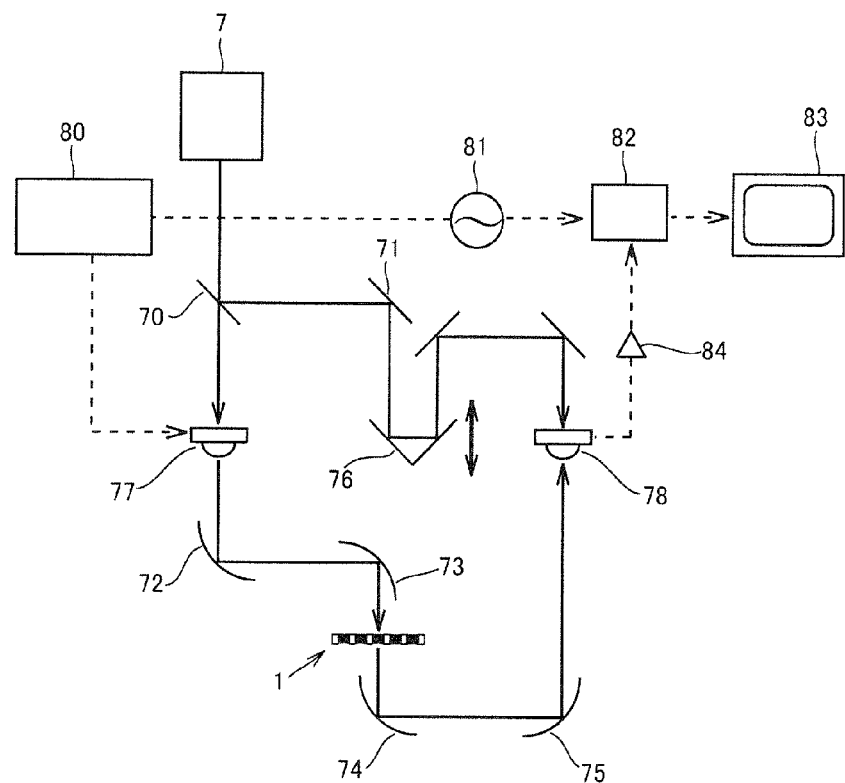
FIG. 1 is a block diagram to explain an outline of a measuring method according to the present invention.

First, an outline of one example of a measuring method according to the present invention will be described below with reference to FIG. 1. FIG. 1 is a block diagram illustrating an overall configuration of a measuring apparatus used to carry out the measuring method according to the present invention. The measuring apparatus utilizes a pulse of an electromagnetic wave (e.g., a terahertz wave having frequency of 20 GHz to 120 THz), which is generated by irradiating a semiconductor material with a laser beam emitted from a laser 7 (e.g., a short optical pulse laser).

In the configuration of FIG. 1, the laser beam emitted from the laser 7 is branched into two paths by a half mirror 70. One of the branched laser beams is applied to a photoconductive element 77 on the electromagnetic wave generation side, and the other laser beam is applied to a photoconductive element 78 on the reception side via a time delay stage 76 by employing a plurality of mirrors 71 (only one of which is denoted by 71 in FIG. 1 with omission of reference numerals for other mirrors having the similar function). The photoconductive elements 77 and 78 can be each prepared using a general photoconductive element that is obtained by forming, in LT-GaAs (low-temperature-grown GaAs), a dipole antenna with a gap portion. The laser 7 may be, e.g., a laser using a solid, such as a fiber type laser or a titanium sapphire laser. The electromagnetic wave can be generated and detected by employing the surface of a semiconductor without an antenna, or an electro-optical crystal such as a ZnTe crystal. A proper bias voltage is applied from a power supply 80 to the gap portion of the photoconductive element 77 on the electromagnetic wave generation side.

The generated electromagnetic wave is converted to a parallel beam through a parabolic mirror 72 and is applied to a periodic structure 1 through a parabolic mirror 73. The terahertz wave having transmitted through the periodic structure 1 is received by the photoconductive element 78 through parabolic mirrors 74 and 75. An electromagnetic signal received by the photoconductive element 78 is amplified by an amplifier 84 and is then obtained as a time waveform in a lock-in amplifier 82. The received electromagnetic signal is subjected to signal processing, such as Fourier transform, in a PC (personal computer) 83 including calculation means, whereby, for example, a transmittance spectrum with the flat-plate periodic structure 1 is calculated. To obtain the time waveform in the lock-in amplifier 82, the bias voltage applied from the power supply 80 to the gap portion of the photoconductive element 77 on the electromagnetic wave generation side is modulated (with an amplitude of 5 V to 30 V) by employing a signal from an oscillator 81. With synchronous detection using the modulated voltage, a signal to noise ratio can be increased.

The above-described measuring method is a method generally called a terahertz time-domain spectroscopy (THz-TDS). A Fourier transform infrared spectroscopy (FT-IR) may be used instead of the THz-TDS.

FIG. 1 illustrates the case of measuring transmittance of an electromagnetic wave. In the present invention, however, reflectance of the electromagnetic wave may be measured. Preferably, the transmittance in the case of transmission in the 0-th order direction or the reflectance in the case of reflection in the 0-th order direction is measured.

In general, given that a lattice interval of a grating is s, an incidence angle is i, a diffraction angle is θ, and a wavelength is λ, a spectrum diffracted by the grating can be expressed by:

$$s(\sin i - \sin \theta) = n\lambda \quad (1)$$

The "0-th order" in the above-mentioned term "0-th order direction" implies the case where n in the above formula (1) is 0. Because s and λ cannot take 0, n=0 holds only when sin i−sin θ=0 is satisfied. Thus, the "0-th order direction" implies the direction given when the incidence angle and the diffraction angle are equal to each other, i.e., when a propagating direction of the electromagnetic wave is not changed.

The electromagnetic wave used in the measuring method according to the present invention is preferably an electromagnetic wave (terahertz wave) having a wavelength λ of 0.3 μm to 15 mm (frequency: 20 GHz to 1 PHz). In order to realize the measurement with higher sensitivity, it is preferable to make shorter the wavelength λ of the electromagnetic wave applied to the aperture array structure. Thus, the wavelength λ is preferably set to be not longer than 300 μm (frequency: not lower than 1 THz).

One practical example of the electromagnetic wave is a terahertz wave that is generated with the optical rectification effect of an electro-optical crystal, e.g., ZnTe, by employing a short optical pulse laser as a light source. Another example of the terahertz wave is one that is generated by exciting free electrons in a photoconductive antenna with a short optical pulse laser used as a light source, and by causing a current to be momentarily generated upon application of a voltage to the photoconductive antenna. Still another example of the terahertz wave is one radiated from, e.g., a high-pressure mercury lamp or a high-temperature ceramic. Other practical examples of the electromagnetic wave include, e.g., visible lights emitted from a semiconductor laser and a photodiode.

In addition, the electromagnetic wave applied to the aperture array structure in the measuring method according to the present invention is preferably a linearly polarized electromagnetic wave. The linearly polarized electromagnetic wave may be a linearly polarized electromagnetic wave obtained after an electromagnetic wave emitted from a light source for non-polarized or circularly-polarized light, for example, has passed through a (linear) polarizer, or a linearly polarized electromagnetic wave emitted from a light source for polarized light. For example, a wire grid can be used as the linear polarizer.

In the present invention, the expression "measuring characteristics of a specimen" implies, e.g., quantitative measurement and qualitative measurement of a compound as the specimen. There are, for example, the case of measuring a minute content of the specimen in, e.g., a solution, and the case of identifying the specimen. More specifically, one exemplary method includes the steps of immersing the aperture array structure in a solution in which the specimen is dissolved, washing a solvent and the extra specimen after the specimen has been attached to the surface of the aperture array structure, drying the aperture array structure, and measuring characteristics of the specimen by employing a measuring apparatus such as described later.

When an amount of the specimen is determined in the present invention, it is preferable to prepare a calibration curve based on frequency characteristics that have been obtained by previously repeating measurement on the specimen in various amounts, and to calculate the amount of the specimen from comparison with the calibration curve.

<Measurement Structure>

(Aperture Array Structure)

The aperture array structure constituting the measurement structure according to the present invention is an aperture array structure having a plurality of aperture portions that penetrate through the aperture array structure in a direction perpendicular to a principal surface thereof. The entirety of the aperture array structure is usually in the form of a flat plate or a film.

The aperture array structure used in the present invention is a structure in which a plurality of aperture portions penetrating through the structure in a direction perpendicular to a principal surface thereof are periodically arrayed in the principal surface at least in one direction. However, the aperture portions are not required to be periodically arrayed over the entirety of the aperture array structure, and they are just required to be periodically arrayed at least in a part of the aperture array structure.

Preferably, the aperture array structure is a quasi-periodic structure or a periodic structure. The term "quasi-periodic structure" implies a structure in which translational symmetry is not held, but an array is orderly kept. Examples of the quasi-periodic structure include a Fibonacci structure as a one-dimensional quasi-periodic structure, and a Penrose structure as a two-dimensional quasi-periodic structure. The term "periodic structure" implies a structure having spatial symmetry such as represented by translational symmetry. The periodic structure is classified into a one-dimensional periodic structure, a two-dimensional periodic structure, and a three-dimensional periodic structure depending on the dimension of the symmetry. The one-dimensional periodic structure is, for example, a wire grid structure or a one-dimensional grating. The two-dimensional periodic structure is, for example, a mesh filter or a two-dimensional grating. Of those periodic structures, the two-dimensional periodic structure is preferably employed. More preferably, a two-dimensional periodic structure including aperture portions regularly arranged in a vertical direction and a horizontal direction (i.e., in a quadrate array) is employed.

Figure 3:
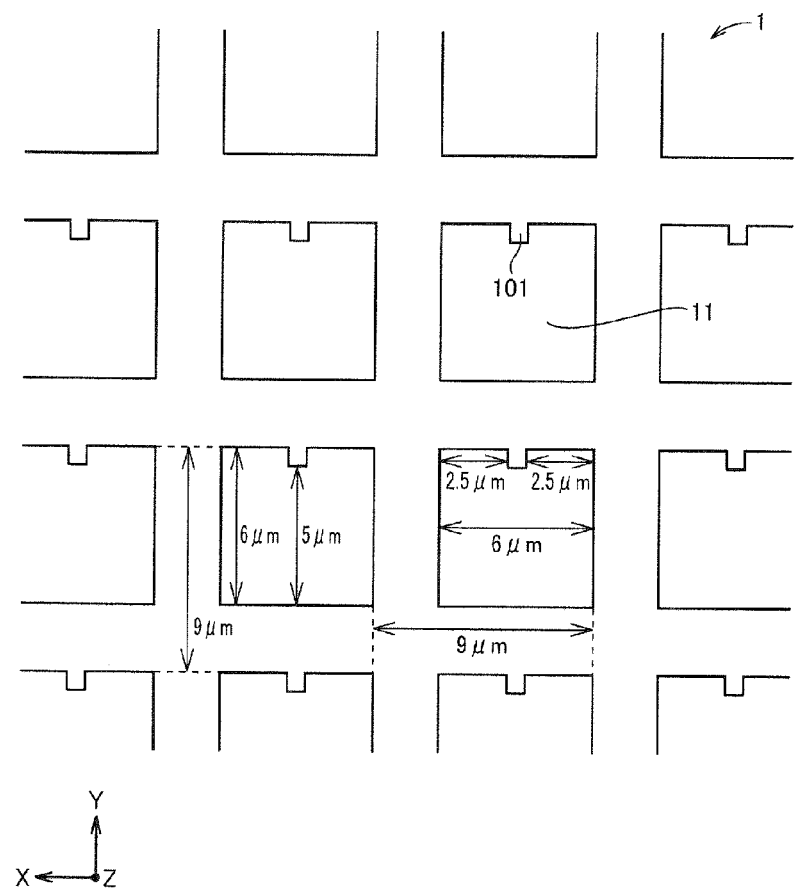
FIG. 3 is a schematic view to explain a lattice structure pattern of an aperture array structure, the view representing an upper surface thereof.

One example of the two-dimensional periodic structure including the aperture portions regularly arranged in the quadrate array is a plate-like structure (also called a lattice structure) in which, as illustrated in FIG. 3, aperture portions 11 are arrayed at constant intervals in a matrix pattern. An aperture array structure 1, illustrated in FIG. 3, is a plate-like structure in which the aperture portions 11, each having a square shape when viewed from the side including a principal surface 10a of the aperture array structure and being provided with a projection 101 in a part of the square shape, are formed at equal intervals in two array directions (i.e., the vertical direction and the horizontal direction in FIG. 3), which are parallel to orthogonal sides of the square shape. It is to be noted that the shape of the aperture portion is not limited to the square shape, and it may be, for example, rectangular, circular, or elliptic. Moreover, insofar as the aperture portions 11 are arranged in the quadrate array, the intervals in the two array directions may not be equal to each other, and the aperture portions 11 may be arranged in a rectangular array.

A thickness (t) of the aperture array structure is preferably a few tenth of the wavelength λ of the electromagnetic wave used in the measurement. For example, when the wavelength λ of the applied electromagnetic wave is 30 μm, t is preferably not more than 150 μm. If the thickness of the structure exceeds such a range, the intensity of the electromagnetic wave transmitting through or reflected by the structure would be so weakened as to cause a difficulty in detecting the signal in some cases.

A size of each aperture portion of the aperture array structure is preferably not less than 1/10 and not more than 10 times the wavelength λ of the electromagnetic wave used in the measurement. If the size of the aperture portion is outside the above-mentioned range, the intensity of the electromagnetic wave transmitting through the structure would be so weakened as to cause a difficulty in detecting the signal in some cases.

A lattice interval (pitch) between the aperture portions is preferably not less than 1/10 and not more than 10 times the wavelength of the electromagnetic wave used in the measurement. If the lattice interval between the aperture portions is outside the above-mentioned range, the electromagnetic wave would be hard to transmit through the structure in some cases.

The shape and the size of the aperture portion of the aperture array structure is designed, as appropriate, depending on the measuring method, the material characteristics of the aperture array structure, the frequency of the electromagnetic wave used, and so on. It is hence difficult to generalize respective ranges of those parameters, and the ranges of those parameters are not limited to the above-mentioned ranges.

The aperture array structure is made of a metal. Examples of the metal include a metal capable of being bonded to a functional group, such as a hydroxy group, a thiol group, or a carboxyl group, of a compound containing that functional group, a metal allowing a functional group, such as a hydroxy group or an amino group, to be coated on the surface of the metal, and an alloy of those metals. Practical examples of the metals are gold, silver, copper, iron, nickel, chromium, silicon, germanium, etc. Of those examples, gold, silver, copper, nickel, and chromium are preferable. Nickel and gold are more preferable.

Using gold or nickel is advantageous in that, particularly when the specimen contains a thiol group (—SH group), the thiol group can be coupled to the surface of the aperture array structure. Furthermore, using nickel is advantageous in that, particularly when the specimen contains a hydroxy group (—OH) or a carboxyl group (—COOH), such a functional group can be coupled to the surface of the aperture array structure.

Although the aperture array structure can be fabricated using various types of known methods, it is preferably formed on the surface of a plate- or film-like support base by the so-called patterning. The patterning can be performed by, e.g., an ordinary process of forming an electrode on a semiconductor (the process including, for example, the steps of coating a resist, printing a pattern, forming a resist pattern, vapor-depositing a metal, and removing the resist).

In the present invention, the specimen can be held on the aperture array structure by optionally employing various known methods. For example, the specimen may be directly attached to the aperture array structure or may be attached to the aperture array structure with, e.g., a support film interposed therebetween. However, the specimen is preferably directly attached to the surface of the aperture array structure from the viewpoint of improving measurement sensitivity and reducing variations in the measurement, thereby performing the measurement with higher reproducibility.

Direct attachment of the specimen to the aperture array structure includes not only the case where chemical coupling, for example, is directly formed between the surface of the aperture array structure and the specimen, but also the case where an aperture array structure having the surface to which a host molecule is coupled in advance is employed and the specimen is coupled to the host molecule. Examples of the chemical coupling include covalent coupling (e.g., covalent coupling between a metal and a thiol group), Van der Waals coupling, ionic coupling, metal coupling, and hydrogen coupling. Of those examples, the valence coupling is preferable. The term "host molecule" implies a molecule to which the specimen can be specifically coupled. Combinations of the host molecule and the specimen are, for example, an antigen and an antibody, a sugar chain and a protein, a lipid and a protein, a low-molecule compound (ligand) and a protein, a protein and a protein, as well as a single strand DNA and a single strand DNA.

(Support Base)

The support base is selected as a member capable of holding the aperture array structure in a state under tension. The expression "state under tension" implies just a state not flexed. The support base is separate from the aperture array structure.

Materials of the support base include, for example, a semiconductor, resin, ceramic, glass, quartz, and so on. Preferably, the material has a high transmittance with respect to the electromagnetic wave used. A preferable material for a terahertz wave or an infrared electromagnetic wave is a semiconductor. Examples of the semiconductor include a group IV semiconductor (e.g., Si or Ge), and compound semiconductors, e.g., a group II-VI semiconductor (e.g., ZnSe, CdS or ZnO), a group III-V semiconductor (e.g., GaAs, InP or GaN), a group IV compound semiconductor (e.g., SiC or SiGe), and a group I-III-VI semiconductor (e.g., $CuInSe_2$), as well as organic semiconductors. Among those examples, silicon (Si) is preferable. When the support base is made of silicon, the support base having the desired shape can be easily fabricated using general-purpose semiconductor techniques such as the MEMS technique. For electromagnetic waves in near infrared and visible ranges, preferable materials of the support base are, e.g., ceramic, glass, and quartz. When the support base is made of a material containing, as a main component, a silicon compound such as glass or quartz, the support base having the desired shape can be easily fabricated using the general-purpose techniques such as the MEMS technique.

In the measurement structure according to the present invention, at least a part of a principal surface of the aperture array structure on the side closer to the support base is joined to the support base, and at least a part of one of principal surfaces of the aperture portion in the aperture array structure, the one principal surface being positioned on the side closer to the support base, is not contacted with the support base.

Figure 2:
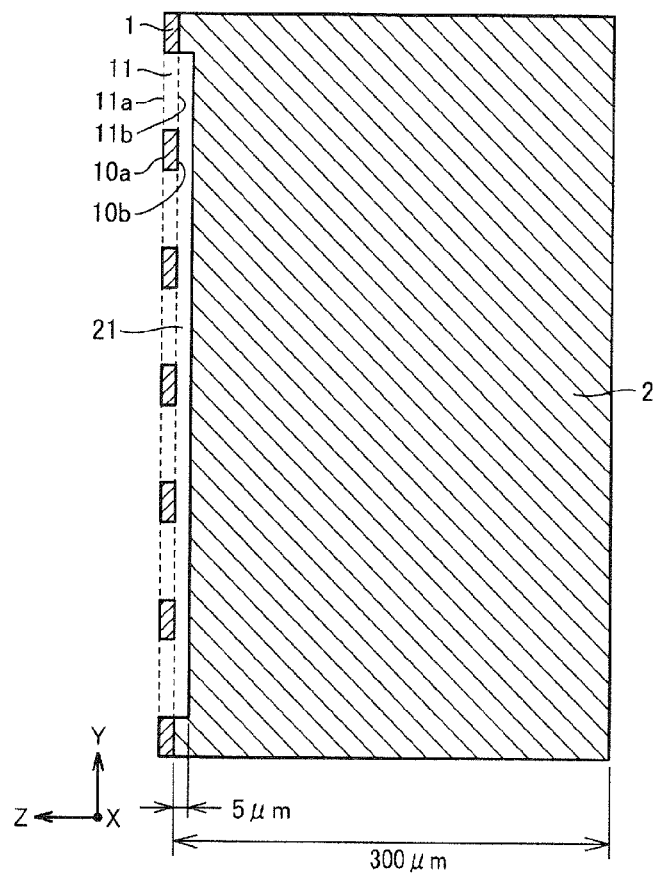
FIG. 2 is a schematic sectional view illustrating one example of a measurement structure according to the present invention.

Here, the expression "principal surface of the aperture array structure" does not imply a plane, but it implies a region of outer peripheral surfaces of the aperture array structure, the region being parallel to the array direction of the aperture portions (e.g., one of principal surfaces 10a and 10b illustrated in FIG. 2). Of the principal surfaces 10a and 10b, the principal surface on the side closer to the support base is, for example, the principal surface 10b illustrated in FIG. 2.

Furthermore, the expression "principal surfaces of the aperture portion in the aperture array structure" implies "principal surfaces of the aperture portion when the aperture portion is assumed to be a member surrounded by respective planes including the principal surfaces of the aperture array structure and by inner lateral surfaces of the aperture array structure". In other words, the expression "principal surfaces of the aperture portion in the aperture array structure" implies "regions of the respective planes including the principal surfaces of the aperture array structure except for the principal surfaces of the aperture array structure, the regions not including outer side portions than the aperture array structure in the direction of those planes" (e.g., principal surfaces 11a and 11b illustrated in FIG. 2). Of the principal surfaces 11a and 11b, the principal surface on the side closer to the support base is, for example, the principal surface lib illustrated in FIG. 2.

As a form in which at least a part of the principal surface of the aperture array structure on the side closer to the support base is joined to the support base, there is, for example, the case where only a peripheral portion of the principal surface of the aperture array structure on the side closer to the support base is joined to the support base. However, such a form is not limited to that case, and the principal surface of the aperture array structure on the side closer to the support base may be entirely joined to the support base.

The support base thus structured is fabricated by a manufacturing method that includes a step of, after forming the aperture array structure on the surface of the plate- or film-like support base as described above, cutting away the support base in a direction of thickness thereof with etching progressed through the aperture portions of the aperture array structure, thereby forming one or more recesses.

Figure 8:
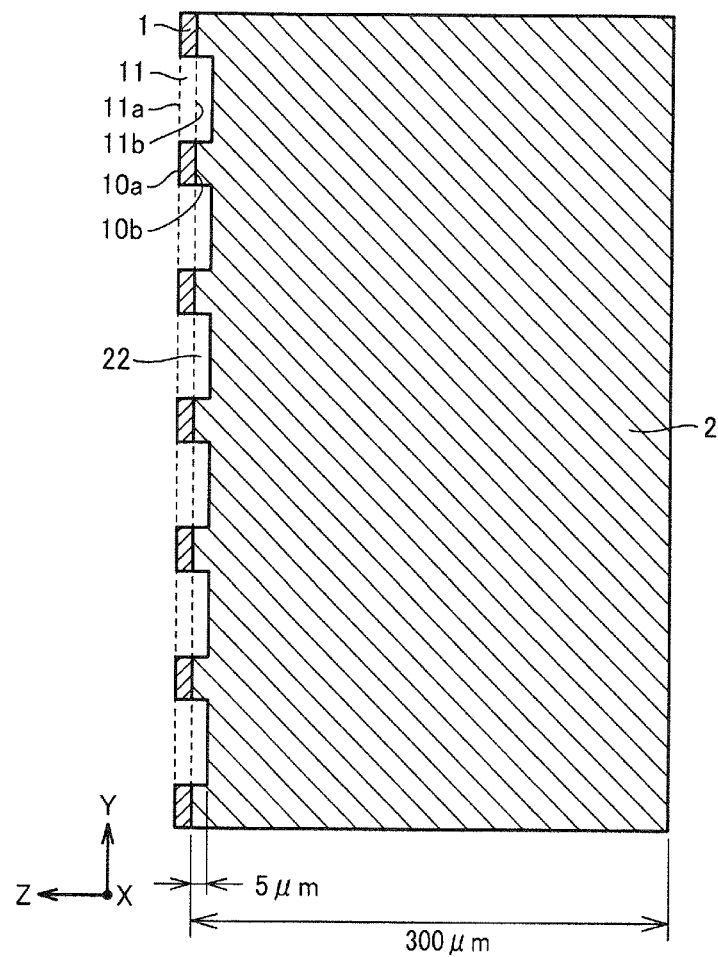
FIG. 8 is a schematic sectional view illustrating another example of the measurement structure according to the present invention.

The "etching progressed through the aperture portions" can be practiced by various types of known etching processes using the aperture array structure as a mask. For example, the general-purpose semiconductor techniques such as the MEMS technique can be used. With those etching processes, it is possible not only to fabricate a support base 2 in which recesses 22 are formed only at positions corresponding to the aperture portions 11, as illustrated in FIG. 8, but also to form a recess 21 in a region (e.g., between the principal surface 10b of the aperture array structure 1 and the support base 2 in FIG. 2) including positions other than the positions corresponding to the aperture portions 11, as illustrated in FIG. 2, by employing an appropriate chemical etching process, for example.

The support base used in the present invention is not limited to a shape having opposite principal surfaces parallel to each other, and the support base may have such a shape that one of the principal surfaces of the support base is inclined at a certain angle relative to the principal surface of the aperture array structure in its aperture array portion when the aperture array structure is in a state held on the support base. The support base having the latter shape is advantageous when the electromagnetic wave is incident on the aperture array structure at a certain incidence angle (i.e., in a state forming a certain angle between a propagating direction of the electromagnetic wave and the principal surface of the aperture array structure).

<Measuring Method>

Preferably, a dip waveform appears in frequency characteristics, such as a transmittance spectrum, which is obtained with the measuring method of the present invention. Here, the term "dip waveform" implies a local reverse peak that usually appears in a frequency region (bandpass region) of the transmittance spectrum, for example, where the transmittance of the electromagnetic wave is high.

The dip waveform appearing in the frequency characteristics is preferably generated with TE11-mode resonance of the aperture array structure (when each aperture portion is regarded as a waveguide). As an alternative, the dip waveform is preferably generated with reduction of TE10-mode resonance of the aperture array structure (when each aperture portion is regarded as a waveguide). The reason is that the dip waveform appearing in the frequency characteristics is sharpened and sensitivity in measurement of the specimen is increased.

In order to generate the dip waveform, the aperture array structure is preferably inclined relative to the propagating direction or the polarizing direction of the electromagnetic wave. Moreover, the dip waveform due to the TE11-mode resonance can also be generated by making the shape of the aperture portion in the aperture array structure not mirror symmetric with respect to an imaginary plane, which is perpendicular to the polarizing plane of the electromagnetic wave. In such a case, the dip waveform due to the TE11-mode resonance can be generated even when the aperture array structure is arranged perpendicularly to the propagating direction of the electromagnetic wave.

The above-mentioned mirror-asymmetric shape of the aperture portion is, for example, a shape including a projection or a cutout in a region defining the aperture portion of the periodic structure. In such a case, it is preferable that, in the region defining the aperture portion of the periodic structure, the projection is present at a position where the intensity of an electric field is relatively strong, or the cutout is present at a position where the intensity of an electric field is relatively weak, when the TE11-mode-like resonance is generated. As an alternative, the aperture portion may be formed to have a trapezoidal, convex, concave, polygonal, or a star-like shape when viewed from a direction perpendicular to the principal surface of the periodic structure, and the aperture array structure may be arranged such that the shape of the aperture portion of the aperture array structure is not mirror symmetric with respect to the imaginary plane, which is perpendicular to the polarizing plane of the electromagnetic wave.

The measuring method has been described above in connection with the case of detecting the frequency characteristics of the electromagnetic wave that has transmitted through the aperture array structure. On the other hand, in the case of detecting the frequency characteristics of the electromagnetic wave that has been reflected by the aperture array structure, the dip waveform in the transmission spectrum appears as a peak waveform in a reflection spectrum.

EXAMPLES

The present invention will be described in more detail below in connection with EXAMPLES, but the present invention is not limited to the following EXAMPLES.

Example 1

A Si semiconductor substrate was prepared as the support base, and the aperture array structure was fabricated on the support base by the ordinary process of forming an electrode on a semiconductor (the process including, for example, the steps of coating a resist, printing a pattern, forming a resist pattern, vapor-depositing a metal, and removing the resist). The measurement structure of the present invention was then obtained by cutting away the support base in the direction of thickness thereof, thus forming a recess, with etching progressed through the aperture portions of the aperture array structure.

FIG. 2 is a schematic sectional view of the measurement structure. The support base 2 is made of Si and has a thickness (including the recess 21) of 300 μm in the Z-direction. As illustrated in FIG. 2, the recess 21 having a depth of 5 μm is formed in a surface of the support base 2 on the side closer to the aperture array structure 1, and the support base 2 is joined to only a periphery of the aperture array structure 1. The aperture array structure 1 is made of Ni and has a thickness of 2 μm. Herein, of the principal surfaces 10a and 10b of the aperture array structure 1, the principal surface 10b on the side closer to the support base 2 is joined at its peripheral portion to the support base 2, and of the principal surfaces 11a and 11b of the aperture portion 11 of the aperture array structure 1, the principal surface 11b on the side closer to the support base 2 is entirely not contacted with the support base 2. Moreover, in this EXAMPLE, other portions of the principal surface 10b of the aperture array structure 1 than the peripheral portion thereof are also not contacted with the support base 2.

FIG. 3 is a partial upper plan view of the aperture array structure 1. The electromagnetic wave incident on the measurement structure is a plane wave polarized in the Y-direction, and is applied to perpendicularly enter the principal surface (XY plane) of the aperture array structure. As illustrated in FIG. 3, the shape of the aperture portion 11 of the aperture array structure is substantially square when viewed from the direction facing the principal surface, with a projection 101 projecting from one side of the square shape. Stated in another way, the aperture portion has such a shape that the projection 101 of 1 μm square projects from one side of a regular square shape of 6 μm square. Respective sizes of various parameters are as per illustrated in FIG. 3. By making the shape of the aperture portion of the aperture array structure not mirror symmetric with respect to an imaginary plane, which is perpendicular to the polarizing plane of the electromagnetic wave, the dip waveform due to the TE11-mode resonance can be generated. In the aperture array structure, the aperture portions, each constituted as described above, are arrayed in a lattice pattern at a lattice interval of 9 μm in each of the vertical direction and the horizontal direction.

Figure 4:
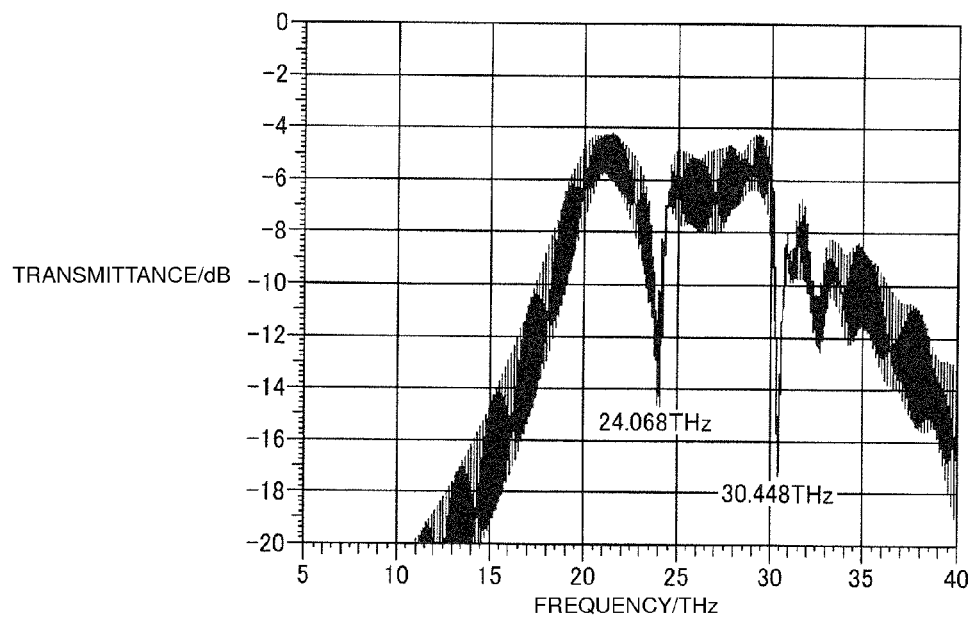
FIG. 4 is a graph depicting a transmittance spectrum (without a specimen to be measured) in Example 1.

FIG. 4 depicts the calculation result (i.e., the result of an electromagnetic field simulation using the FDTD (Finite-difference time-domain) method) of a transmittance spectrum obtained with the measurement structure of this EXAMPLE when the specimen is not held thereon. As seen from FIG. 4, a dip waveform attributable to the aperture array structure is observed at 24.068 THz. It is to be noted that, although minute peaks other than the dip waveform, etc. are also recorded in the graph of FIG. 4, those minute peaks are generated by interference caused by the support base and are negligible when the characteristics of the specimen are measured (this is similarly applied to other graphs).

Figure 5:
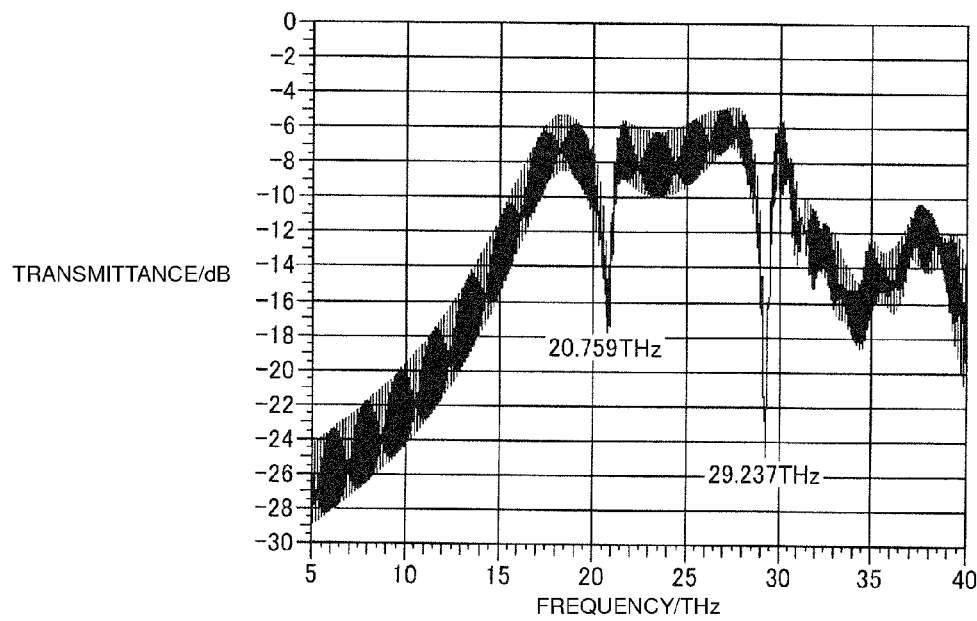
FIG. 5 is a graph depicting a transmittance spectrum (with the specimen) in Example 1.

FIG. 5 depicts the calculation result of a transmittance spectrum obtained when a dielectric film (having a thickness of 500 nm and a refractive index of 2) as the specimen is attached to the principal surface (specifically, the principal surface not facing the support base) of the aperture array structure in the measurement structure of EXAMPLE 1. As seen from FIG. 5, a dip waveform is observed at 20.759 THz. From comparison with FIG. 4, it is understood that a frequency shift (shift amount of 3.309 THz) of the dip waveform occurs due to the presence of the specimen. This implies that the specimen can be detected based on a change of the frequency characteristics by employing the measurement structure of this EXAMPLE.

Comparative Example

Figure 14:
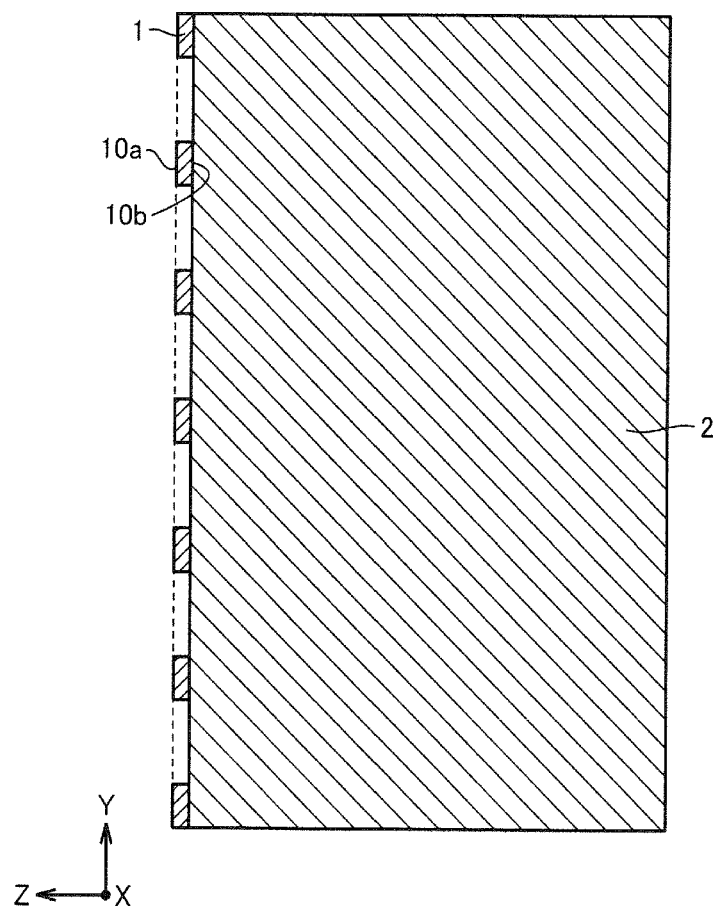
FIG. 14 is a schematic sectional view illustrating one example of a measurement structure according of related art.

The known measurement structure, illustrated in FIG. 14, was fabricated in the same manner as that in EXAMPLE 1 except for that the recess 21 is not formed between the aperture array structure and the support base as illustrated in FIG. 2.

Figure 6:
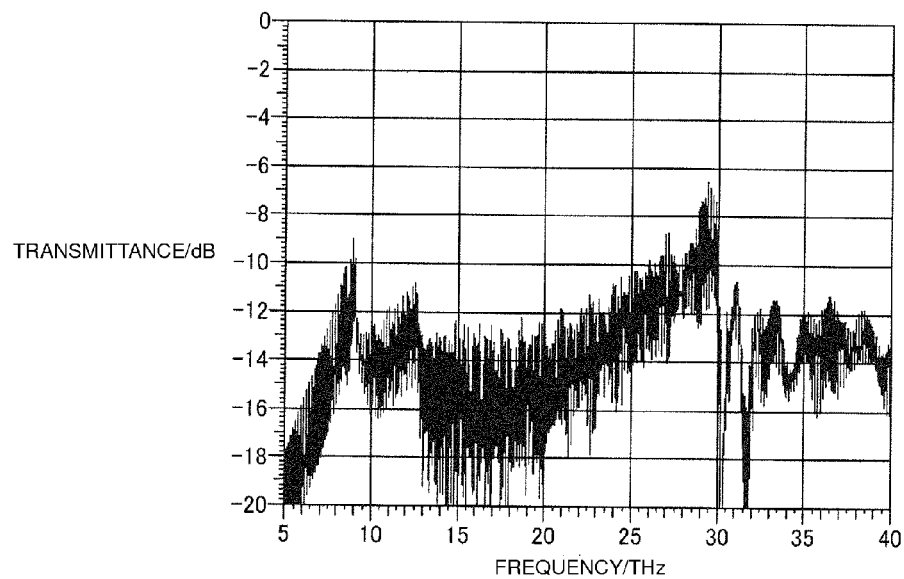
FIG. 6 is a graph depicting a transmittance spectrum (without a specimen to be measured) in Comparative Example 1.

FIG. 6 depicts the calculation result of a transmittance spectrum for the measurement structure of COMPARATIVE EXAMPLE. As seen from FIG. 6, the dip waveform attributable to the aperture array structure, depicted in FIG. 4, is not clearly observed, and the transmittance is comparatively small on the whole.

Figure 7:
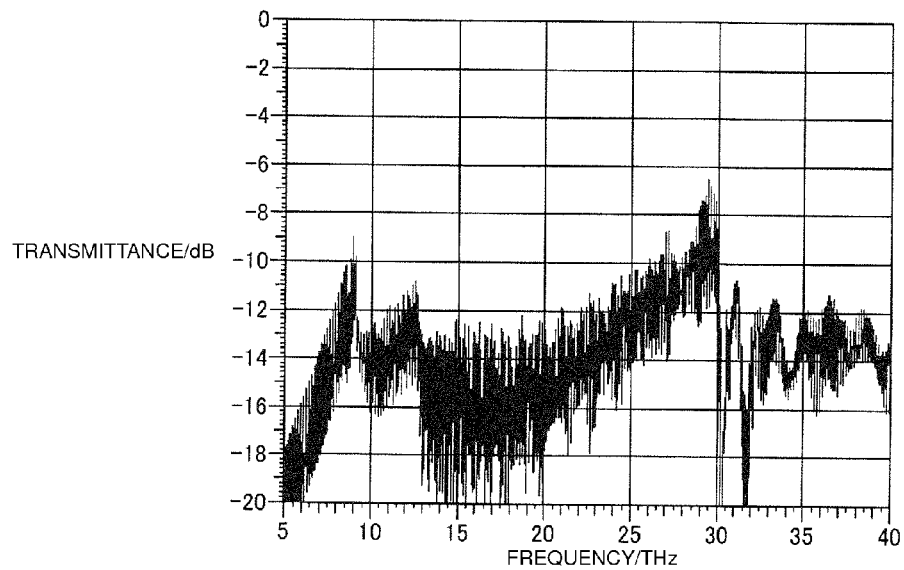
FIG. 7 is a graph depicting a transmittance spectrum (with the specimen) in Comparative Example 1.

FIG. 7 depicts the calculation result of a transmittance spectrum obtained when a dielectric film (having a thickness of 500 nm and a refractive index of 2) as the specimen is attached to the principal surface (specifically, the principal surface not facing the support base) of the aperture array structure in the measurement structure of COMPARATIVE EXAMPLE. From comparison between FIG. 6 and FIG. 7, it is understood that a frequency shift of the dip waveform due to the presence of the specimen cannot be observed.

Example 2

Figure 9:
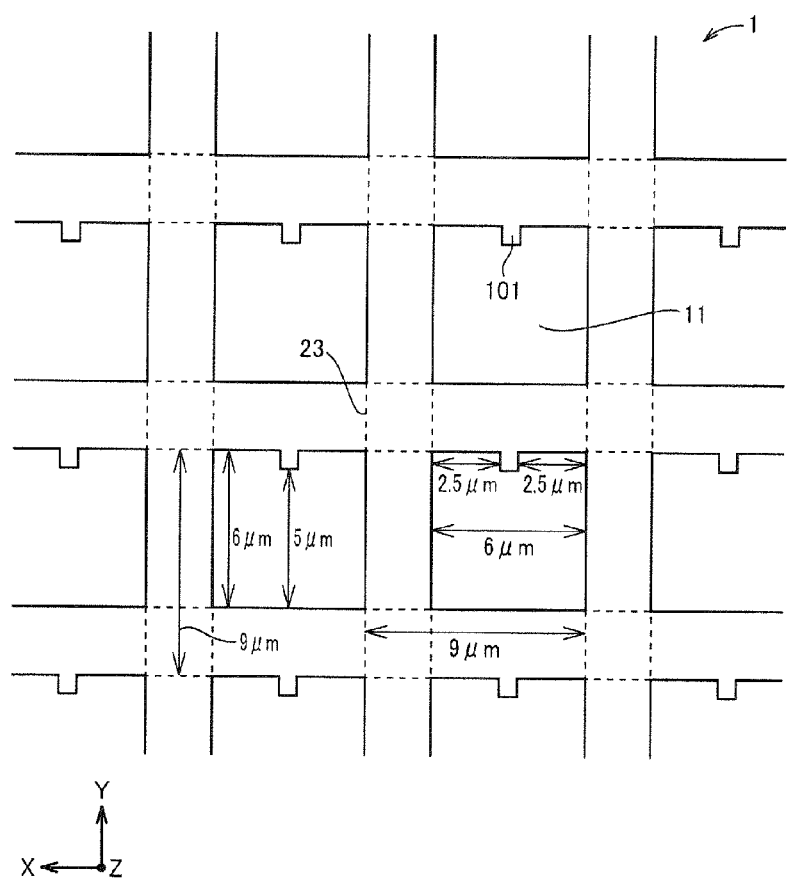
FIG. 9 is a schematic view illustrating the other example of the measurement structure according to the present invention, the view representing an upper surface thereof.

A measurement structure was fabricated in the same manner as that in EXAMPLE 1 except for providing a plurality of posts periodically arranged between the aperture array structure and the support base as illustrated in FIG. 8. In more detail, each of the posts is made of Si, i.e., the same material as that of the support base, and has the shape of a right prism with one side having a length of 3%. The posts 23 are arranged at positions illustrated in FIG. 9 with respect to the aperture array structure 1, and the pitch between the posts 23 is 9 μm, i.e., the same as the lattice interval. Herein, of the principal surfaces 10a and 10b of the aperture array structure 1, the principal surface 10b on the side closer to the support base 2 is joined at its peripheral portion to the support base 2, and of the principal surfaces 11a and 11b of the aperture portion 11 of the aperture array structure 1, the principal surface 11b on the side closer to the support base 2 is entirely not contacted with the support base 2. Moreover, in this EXAMPLE, a portion of the principal surface 10b of the aperture array structure 1 is contacted with the support base 2 in a region corresponding to each post 23.

Figure 10:
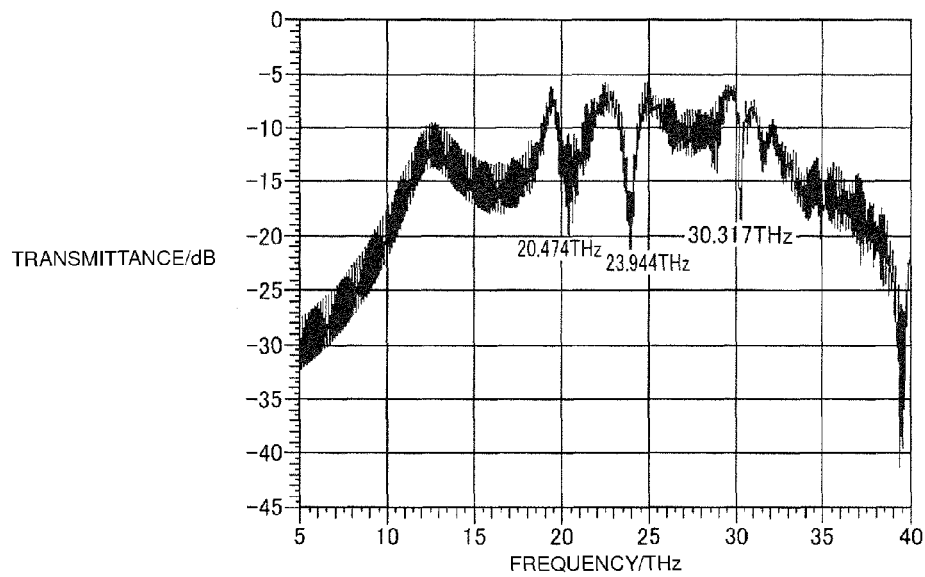
FIG. 10 is a graph depicting a transmittance spectrum (without a specimen to be measured) in Example 2.

FIG. 10 depicts the calculation result of a transmittance spectrum for the measurement structure of Example 2. As seen from FIG. 10, a dip waveform attributable to the aperture array structure is observed at 23.944 THz (other dip waveforms are not attributable to the TE11-mode resonance of the aperture array structure (when each aperture portion is assumed to be a waveguide)).

Figure 11:
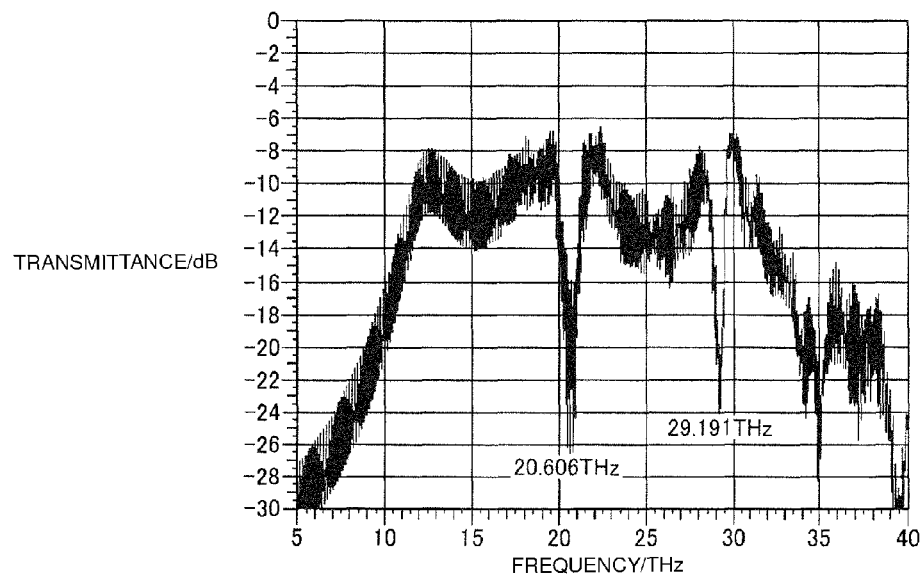
FIG. 11 is a graph depicting a transmittance spectrum (with the specimen) in Example 2.

FIG. 11 depicts the calculation result of a transmittance spectrum obtained when a dielectric film (having a thickness of 500 nm and a refractive index of 2) as the specimen is attached to the principal surface (specifically, the principal surface not facing the support base) of the aperture array structure in the measurement structure of this EXAMPLE. As seen from FIG. 11, a dip waveform is observed at 20.606 THz. From comparison with FIG. 10, it is understood that a frequency shift (shift amount of 3.338 THz) of the dip waveform occurs due to the presence of the specimen. This implies that the specimen can be detected based on a change of the frequency characteristics by employing the measurement structure of this EXAMPLE.

Example 3

A measurement structure was fabricated in the same manner as that in EXAMPLE 1 except for, as illustrated in FIG. 8, forming a recess 22 in the surface of the support base 2 on the side closer to the aperture array structure 1, the recess 22 having a concave shape (like a counterbored shape) in a region obtained by projecting the shape of each aperture portion 11 of the aperture array structure 1 to the support base 2. Herein, of the principal surfaces 10a and 10b of the aperture array structure 1, the principal surface 10b on the side closer to the support base 2 is joined at its peripheral portion to the support base 2, and of the principal surfaces 11a and 11b of the aperture portion 11 of the aperture array structure 1, the principal surface 11b on the side closer to the support base 2 is entirely not contacted with the support base 2. Moreover, in this EXAMPLE, the principal surface 10b of the aperture array structure 1 is entirely contacted with the support base 2.

Figure 12:
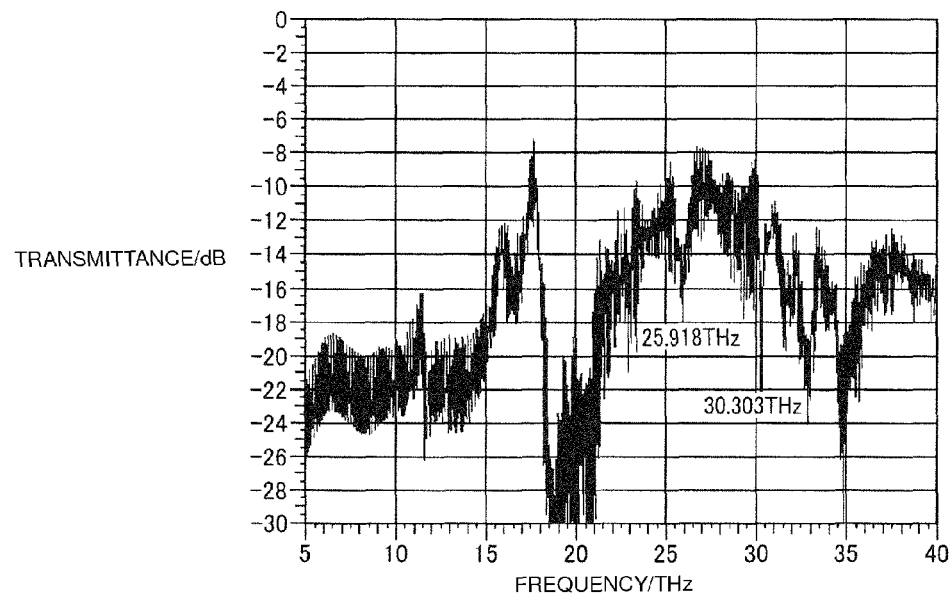
FIG. 12 is a graph depicting a transmittance spectrum (without a specimen to be measured) in Example 3.

FIG. 12 depicts the calculation result of a transmittance spectrum for the measurement structure of Example 3

As seen from FIG. 12, a dip waveform attributable to the aperture array structure is observed at 25.918 THz (other dip waveforms are not attributable to the aperture array structure).

Figure 13:
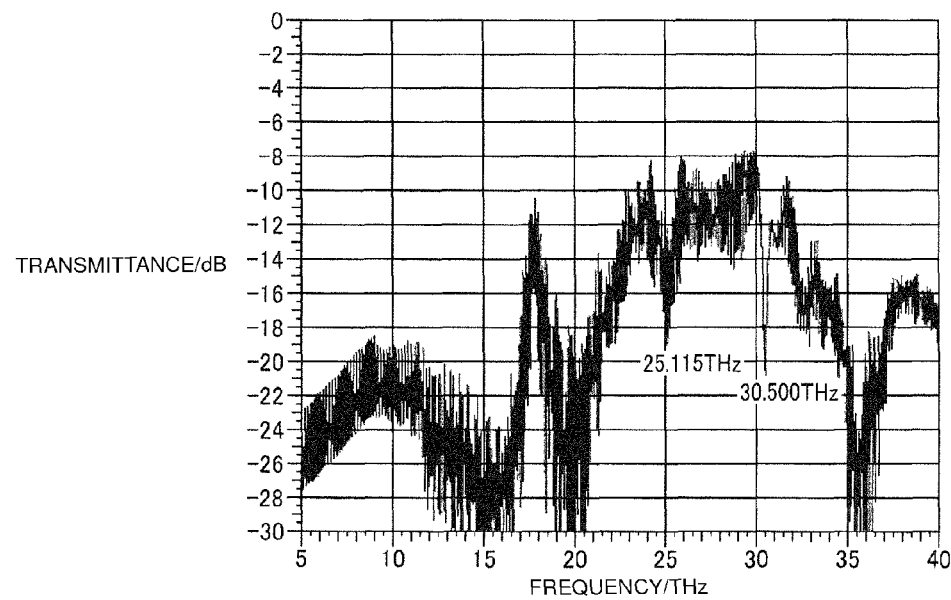
FIG. 13 is a graph depicting a transmittance spectrum (with the specimen) in Example 3.

FIG. 13 depicts the calculation result of a transmittance spectrum obtained when a dielectric film (having a thickness of 500 nm and a refractive index of 2) as the specimen is attached to the principal surface (specifically, the principal surface not facing the support base) of the aperture array structure in the measurement structure of this EXAMPLE. As seen from FIG. 13, a dip waveform is observed at 25.115 THz. From comparison with FIG. 12, it is understood that a frequency shift (shift amount of 0.803 THz) of the dip waveform occurs due to the presence of the specimen. This implies that the specimen can be detected based on a change of the frequency characteristics by employing the measurement structure of this EXAMPLE.

The embodiment and EXAMPLES disclosed above should be construed in all respects as illustrative and not restrictive. The scope of the present invention is defined in claims, but not in the above description, and involves all modifications equivalent to the claims in meaning and scope.

REFERENCE SIGNS LIST 1 aperture array structure, 10a, 10b principal surfaces, 101 projection, 11 aperture portion, 11a, 11b principal surfaces, 2 support base, 21, 22 recesses, 23 post, 7 laser, 70 half mirror, 71 mirror, 72, 73, 74, 75 parabolic mirrors, 76 time delay stage, 77, 78 photoconductive elements, 80 power supply, 81 oscillator, 82 lock-in amplifier, 83 PC (personal computer), and 84 amplifier.

The invention claimed is:

1. A measurement structure comprising:
an aperture array structure defining a plurality of aperture portions; and
a support base joined to a periphery of the aperture array structure,
wherein the plurality of aperture portions are connected to each other in an area defined by a space between the aperture array structure and the support base where the aperture array structure is not in contact with the support base.

2. The measurement structure according to claim 1, wherein the aperture array structure is metal.

3. The measurement structure according to claim 2, wherein the metal is selected from the group consisting of gold, silver, copper, iron, nickel, chromium, silicon, and germanium.

4. The measurement structure according to claim 1, wherein the plurality of aperture portions are periodically arrayed in at least one direction.

5. The measurement structure according to claim 1, wherein a size of each aperture portion of the plurality of aperture portions is not less than $1/10$ and not more than 10 times a wavelength $\lambda$ of an electromagnetic wave used for measurement.

6. The measurement structure according to claim 5, wherein a lattice interval between adjacent aperture portions of the plurality of aperture portions is not less than $1/10$ and not more than 10 times the wavelength $\lambda$ of the electromagnetic wave used for measurement.

7. The measurement structure according to claim 1, wherein a lattice interval between adjacent aperture portions of the plurality of aperture portions is not less than $1/10$ and not more than 10 times the wavelength $\lambda$ of the electromagnetic wave used for measurement.

8. The measurement structure according to claim 1, wherein the support base is a material containing silicon or a silicon compound as a main component.

9. A method of manufacturing a measurement structure, the method comprising:
forming an aperture array structure that includes a plurality of aperture portions on a surface of a support base; and
cutting away the support base in a direction of thickness thereof to form one or more recesses with etching progressed through the aperture portions of the aperture array structure such that the support base is joined to a periphery of the aperture array structure, and the plurality of aperture portions are connected to each other in an area defined by a space between the aperture array structure and the support base where the aperture array structure is not in contact with the support base.

10. The method of manufacturing a measurement structure according to claim 9, wherein the aperture array structure is metal.

11. The method of manufacturing a measurement structure according to claim 10, wherein the metal is selected from the group consisting of gold, silver, copper, iron, nickel, chromium, silicon, and germanium.

12. The method of manufacturing a measurement structure according to claim 9, wherein the plurality of aperture portions are periodically arrayed in at least one direction.

13. The method of manufacturing a measurement structure according to claim 9, wherein a size of each aperture portion of the plurality of aperture portions is not less than $1/10$ and not more than 10 times a wavelength $\lambda$ of an electromagnetic wave used for measurement.

14. The method of manufacturing a measurement structure according to claim 13, wherein a lattice interval between adjacent aperture portions of the plurality of aperture portions is not less than $1/10$ and not more than 10 times the wavelength $\lambda$ of the electromagnetic wave used for measurement.

15. The method of manufacturing a measurement structure according to claim 9, wherein a lattice interval between adjacent aperture portions of the plurality of aperture portions is not less than $1/10$ and not more than 10 times the wavelength $\lambda$ of the electromagnetic wave used for measurement.

16. The method of manufacturing a measurement structure according to claim 9, wherein the support base is a material containing silicon or a silicon compound as a main component.

17. A measuring method comprising:
holding a specimen to be measured in a plurality of aperture portions of a measurement structure that comprises an aperture array structure defining a plurality of aperture portions; and a support base joined to a periphery of the aperture array structure, wherein the plurality of aperture portions are connected to each other in an area defined by a space between the aperture array structure and the support base where the aperture array structure is not in contact with the support base;
applying an electromagnetic wave to the measurement structure on which the specimen is held;
detecting frequency characteristics of the electromagnetic wave having transmitted through the measurement structure or the electromagnetic wave having been reflected by the measurement structure; and
measuring characteristics of the specimen.

18. The measuring method according to claim 17, further comprising inclining the aperture array structure relative to a propagating direction or a polarizing direction of the electromagnetic wave.

* * * * *